United States Patent
Francis (10) Patent No.: US 7,766,967 B2
(45) Date of Patent: Aug. 3, 2010

(54) INTERVERTEBRAL DISC NUCLEUS REPLACEMENT IMPLANTS AND METHODS

(75) Inventor: Thomas J. Francis, Cardova, TN (US)

(73) Assignee: Warsaw Orthopedic Inc., Warsaw, IN (US)

( * ) Notice: Subject to any disclaimer, the term of this patent is extended or adjusted under 35 U.S.C. 154(b) by 527 days.

(21) Appl. No.: 11/398,873

(22) Filed: Apr. 6, 2006

(65) Prior Publication Data

US 2007/0239279 A1  Oct. 11, 2007

(51) Int. Cl.
A61F 2/44 (2006.01)
(52) U.S. Cl. .................................................. 623/17.16
(58) Field of Classification Search ... 623/17.11–17.16; 606/61, 70
See application file for complete search history.

(56) References Cited

U.S. PATENT DOCUMENTS

| | | | |
|---|---|---|---|
| 3,867,728 A | 2/1975 | Stubstad et al. ..................... 3/1 |
| 4,932,969 A | 6/1990 | Frey et al. ....................... 623/17 |
| 6,620,196 B1 | 9/2003 | Trieu ....................... 623/17.16 |
| 6,960,232 B2 * | 11/2005 | Lyons et al. ............. 623/17.16 |
| 7,008,453 B1 * | 3/2006 | Michelson ............... 623/17.16 |
| 7,018,415 B1 | 3/2006 | McKay |
| 2002/0026244 A1 * | 2/2002 | Trieu ....................... 623/17.16 |
| 2002/0111686 A1 * | 8/2002 | Ralph et al. ............. 623/17.13 |
| 2002/0128715 A1 | 9/2002 | Bryan et al. ............. 623/17.15 |
| 2002/0177897 A1 * | 11/2002 | Michelson ............... 623/17.11 |
| 2003/0074074 A1 | 4/2003 | Errico et al. ............. 623/17.14 |
| 2003/0199983 A1 * | 10/2003 | Michelson ............... 623/17.16 |
| 2003/0199984 A1 | 10/2003 | Trieu ....................... 623/17.16 |
| 2004/0093082 A1 | 5/2004 | Ferree |
| 2004/0117019 A1 | 6/2004 | Trieu et al. ............... 623/17.11 |
| 2004/0236425 A1 | 11/2004 | Huang ..................... 623/17.16 |
| 2005/0043796 A1 | 2/2005 | Grant et al. |
| 2005/0187632 A1 | 8/2005 | Zubok et al. ............. 623/17.14 |
| 2005/0228500 A1 | 10/2005 | Kim et al. ................. 623/17.13 |
| 2005/0256576 A1 | 11/2005 | Moskowitz et al. ...... 623/17.12 |

FOREIGN PATENT DOCUMENTS

| WO | WO 2004064693 A1 | 8/2004 |
|---|---|---|
| WO | WO 2004080356 A2 | 9/2004 |
| WO | WO 2005/051246 A2 | 6/2005 |

OTHER PUBLICATIONS

Allard et al., "Instruments and Methods for Implanting Nucleus Replacement Material in an Intervertebral Disc Nucleus Space", U.S. Appl. No. 11/343,088, filed Jan. 30, 2006.
International Search Report, PCT/US2007/065310, dated Sep. 20, 2007 (5 pages).

* cited by examiner

*Primary Examiner*—Eduardo C Robert
*Assistant Examiner*—Elana B Fisher (57) ABSTRACT

Intervertebral disc nucleus replacement implants and methods are provided. The nucleus replacement implant, which is configured to reside within an intervertebral disc nucleus space, includes a core support structure, including a rotatable member and multiple vertebral support structures. The vertebral support structures are disposed in spaced relation with the rotatable member positioned therebetween. The implant further includes an elastic body at least partially surrounding the core support structure. When the rotatable member is in the first orientation, the implant is in a compressed height configuration to facilitate insertion of the implant into the intervertebral disc nucleus space, and when the rotatable member is in the second orientation, the implant is in an extended height configuration to facilitate use of the implant as a prosthetic intervertebral disc nucleus replacement.

25 Claims, 4 Drawing Sheets

INTERVERTEBRAL DISC NUCLEUS REPLACEMENT IMPLANTS AND METHODS

CROSS-REFERENCE TO RELATED APPLICATIONS/PATENTS

This application contains subject matter which is related to the subject matter of the following applications/patents, which are hereby incorporated herein by reference in their entirety:

"Instruments and Methods for Implanting Nucleus Replacement Material in an Intervertebral Disc Nucleus Space", Allard et al., U.S. Ser. No. 11/343,088, filed Jan. 30, 2006;

"Method and Apparatus for Delivering an Intervertebral Disc Implant", Trieu et al., U.S. Ser. No. 10/717,687, filed Nov. 20, 2003, and published on Jun. 17, 2004 as Patent Application Publication No. US 2004/0117019 A1;

"Method and Apparatus for Delivering an Intervertebral Disc Implant", Trieu et al., Patent Cooperation Treaty Application No. PCT/US2004/038750, and published on Jun. 9, 2005 as International Publication No. WO 2005/051246 A2;

"Intervertebral Disc Nucleus Implants and Methods", Hai H. Trieu, U.S. Ser. No. 09/943,411, filed Aug. 30, 2001, and published on Feb. 28, 2002 as Patent Application Publication No. US 2002/0026244 A1;

"Intervertebral Disc Nucleus Implants and Methods" Hai H. Trieu, U.S. Ser. No. 10/459,630, filed Jun. 11, 2003, and published on Oct. 23, 2003 as Patent Application Publication No. US 2003/0199984 A1; and "Intervertebral Disc Nucleus Implants and Methods", Hai H. Trieu, U.S. Pat. No. 6,620,196 B1, issued Sep. 16, 2003.

TECHNICAL FIELD

The present invention relates generally to spinal implants and methods, and more particularly, to prosthetic nucleus replacement implants and methods to augment, repair, or replace an intervertebral disc nucleus.

BACKGROUND OF THE INVENTION

The human spine is a biomechanical structure with thirty-three vertebral members, and is responsible for protecting the spinal cord, nerve roots and internal organs of the thorax and abdomen. The spine also provides structure support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

The intervertebral disc functions to stabilize the spine and to distribute forces between vertebral bodies. A normal disc includes a gelatinous nucleus pulposus, an annulus fibrosis and two vertebral endplates. The nucleus pulposus is surrounded and confined by the annulus fibrosis between the vertebral endplates.

It is known that intervertebral discs are prone to injury and degeneration. For example, herniated discs are common, and typically occur when normal wear, or exceptional strain, causes a disc to rupture. Degenerative disc disease typically results from the normal aging process, in which the tissue gradually looses its natural water and elasticity, causing the degenerated disc to shrink and possibly rupture.

Intervertebral disc injuries and degeneration are frequently treated by replacing or augmenting the existing disc material. Current intervertebral disc replacement procedures tend to utilize full-sized implants, particularly hydrogels, to augment or replace the original disc nucleus. These materials are commonly implanted after first making a hole with a guide wire, and then subsequently enlarging the hole with a succession of sleeves having increased diameters. Alternatively, a larger hole may be made by surgical incision, using a scalpel or a small diameter coring blade.

One problem with such implants is that they require a relatively large hole to be cut in the disc annulus to allow introduction of the implant. Since the hole must be large enough to accommodate a full sized implant, the annulus must be plugged or sewn closed after implantation to avoid allowing the implant to be expelled from the disc. This complicates the procedure, adding surgical time and cost, and leaving a less sound annulus when the procedure is complete.

Another problem with such implants is the possibility of tearing or otherwise damaging the hydrogel implant during implantation. Moreover, once positioned in the disc space, many hydrogel implants may migrate in the disc space and/or may be expelled from the disc space through an annular defect, or other annular opening.

A need therefore exists for more durable implants, as well as implants that are resistant to migration and/or expulsion through an opening in the annulus fibrosis. The devices and methods disclosed herein address these needs.

SUMMARY OF THE INVENTION

The shortcomings of the prior art are overcome and additional advantages are provided, in one aspect, through provision of an intervertebral disc nucleus replacement implant configured to reside within an intervertebral disc nucleus space. The nucleus replacement implant includes a core support structure comprising a rotatable member and an elastic body comprising biocompatible material at least partially surrounding the core support structure. The rotatable member is rotatable between a first orientation and a second orientation. When the rotatable member is in the first orientation, the nucleus replacement implant is in a compressed height configuration of height H1 to facilitate insertion of the implant into the intervertebral disc nucleus space, and when the rotatable member is in the second orientation, the nucleus replacement device is in an extended height configuration of height H2, wherein H2>H1, to facilitate use of the implant as a prosthetic intervertebral disc nucleus replacement.

In certain enhanced aspects, the rotatable member of the nucleus replacement implant has a first width W1 in a first dimension and a second width W2 in a second dimension, with W2>W1, and wherein when the nucleus replacement implant is disposed within the intervertebral disc nucleus space and the rotatable member is in the first orientation, width W1 of the rotatable member is oriented substantially vertical within the intervertebral disc nucleus space, and when in the second orientation, width W2 of the rotatable member is oriented substantially vertical. Further, the rotatable member may comprise one of: a barrel-shaped member, a cam-shaped member, a cylindrical-shaped member, an elliptical-shaped member, a rectangular-shaped member, or a tubular-shaped member, etc. The rotatable member, which can be fabricated of metal, a non-elastic biocompatible material, or an elastic polymer of higher stiffness than the surrounding elastic body, includes at least one opening configured for facilitating rotating of the rotatable member once positioned within the intervertebral disc nucleus space. Still further, the elastic body of the nucleus replacement implant may include a centrally-disposed chamber comprising intersecting horizontally oriented and vertically oriented chambers. With such a structure, the rotatable member is in the first orientation when positioned within the horizontally oriented chamber, and is in the second orientation when positioned within the vertically oriented chamber. The elastic body defines the horizontally oriented chamber and the vertically oriented chamber, and assists in maintaining the rotatable member in one of the first orientation and the second orientation.

In another aspect, an intervertebral disc nucleus replacement implant is provided configured to reside within an intervertebral disc nucleus space. This implant includes a core support structure comprising a rotatable member and two vertebral support structures. The rotatable member is rotatable between a first orientation and a second orientation, and the vertebral support structures are disposed in spaced relation with the rotatable member positioned therebetween. The implant further includes an elastic body comprising biocompatible material at least partially surrounding the core support structure. When the rotatable member is in the first orientation, the nucleus replacement implant is in a compressed height configuration of height H1 to facilitate insertion of the nucleus replacement implant into the intervertebral disc nucleus space, and when the rotatable member is in the second orientation, the nucleus replacement implant is in an extended height configuration of height H2, wherein H2>H1, to facilitate use of the nucleus replacement implant as a prosthetic intervertebral disc nucleus replacement.

In a further aspect, a method of providing a prosthetic intervertebral disc nucleus replacement is presented. This method includes providing a nucleus replacement implant configured to reside within an intervertebral disc nucleus space. The nucleus replacement implant includes a core support structure comprising a rotatable member that is rotatable between a first orientation and a second orientation. The implant further includes an elastic body comprising biocompatible material at least partially surrounding the core support structure. When the rotatable member is in the first orientation, the nucleus replacement implant is in a compressed height configuration of height H1 to facilitate insertion of the nucleus replacement implant into the intervertebral disc nucleus space, and when the rotatable member is in the second orientation, the nucleus replacement implant is in an extended height configuration of H2, wherein H2>H1, to facilitate use of the nucleus replacement implant as a prosthetic intervertebral disc nucleus replacement. The method further includes: preparing the intervertebral disc nucleus space to receive the nucleus replacement device, the preparing including providing a hole in an annulus of the intervertebral disc nucleus space, the hole having a size sufficient to allow passage of the nucleus replacement implant therethrough in the compressed height configuration; positioning the nucleus replacement implant in the intervertebral disc nucleus space by inserting the nucleus replacement implant in the compressed height configuration through the hole in the annulus of the intervertebral disc nucleus space; and once positioned within the intervertebral disc nucleus space, rotating the rotatable member to the second orientation so that the nucleus replacement implant is in the extended height configuration.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

BEST MODE FOR CARRYING OUT THE INVENTION

Generally stated, prosthetic intervertebral disc nucleus pulposus implants are presented herein which may fully or partially replace the natural, or native, nucleus pulposus in mammals, including humans or other animals. The implants described herein are configured to resist expulsion or other migration through a defect, or other opening, in the annulus fibrosis and to resist excessive migration within the intervertebral disc space. Although described herein as including a preformed, elastic body comprising biocompatible material, the implants may further be combined with an injectable/in-situ curing material, either with or without a preformed body. For example, a nucleus pulposus implant may include a load bearing replacement device, referred to herein as the core support structure, surrounded by an outer resorbable or otherwise temporary, shell.

The surface of the elastic body (whether preformed or injectable) may include various surface features, including various macro-surface patterns, and chemical or physical modifications to further enhance fixation of the elastic body to surrounding tissue.

In other aspects, the preformed elastic body, of the nucleus pulposus implants described herein, may have shape memory and be configured to allow extensive short term manual or other deformation without permanent deformation, cracks, tears, breakage or other damage. The deformability of the elastic body of biocompatible material allows the implant to pass through a relatively small incision in the annulus fibrosis, and also to substantially fill and conform to an intervertebral disc space.

As noted, in the embodiments described herein, the implant includes a load bearing structure referred to as the core support structure. This structure includes a rotatable member, which is rotatable between a first orientation and a second orientation. When the rotatable member is in the first orientation, the nucleus replacement implant is in a compressed height configuration of height H1 to facilitate insertion of the implant into the intervertebral disc nucleus space, and when the rotatable member is in the second orientation, the nucleus replacement implant is in an extended height configuration of height H2, wherein H2>H1, to facilitate use or functioning of the implant as a prosthetic intervertebral disc nucleus replacement.

Figure 1:
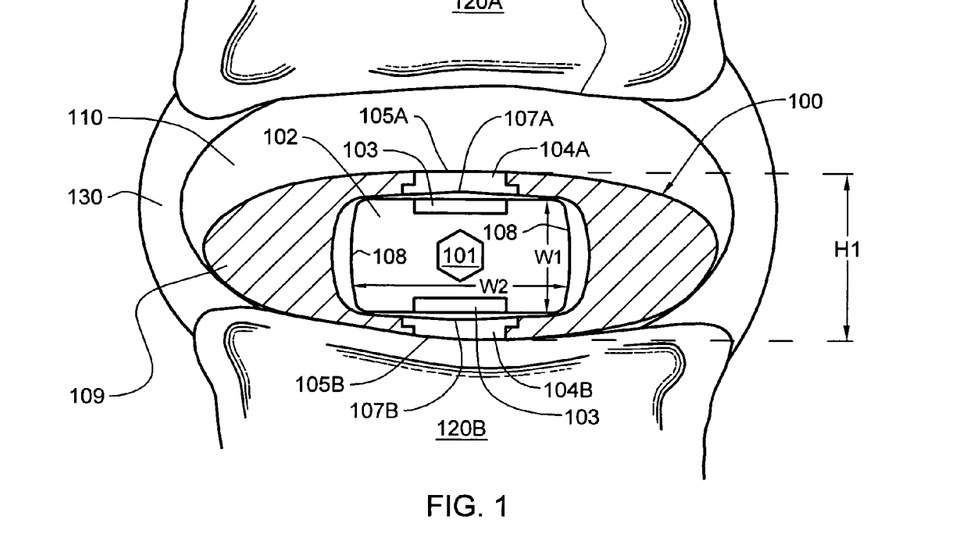
FIG. 1 is a cross-sectional, side elevational view of one embodiment of a nucleus replacement implant in compressed height configuration disposed within an intervertebral disc nucleus space, in accordance with an aspect of the present invention.
Figure 1A:
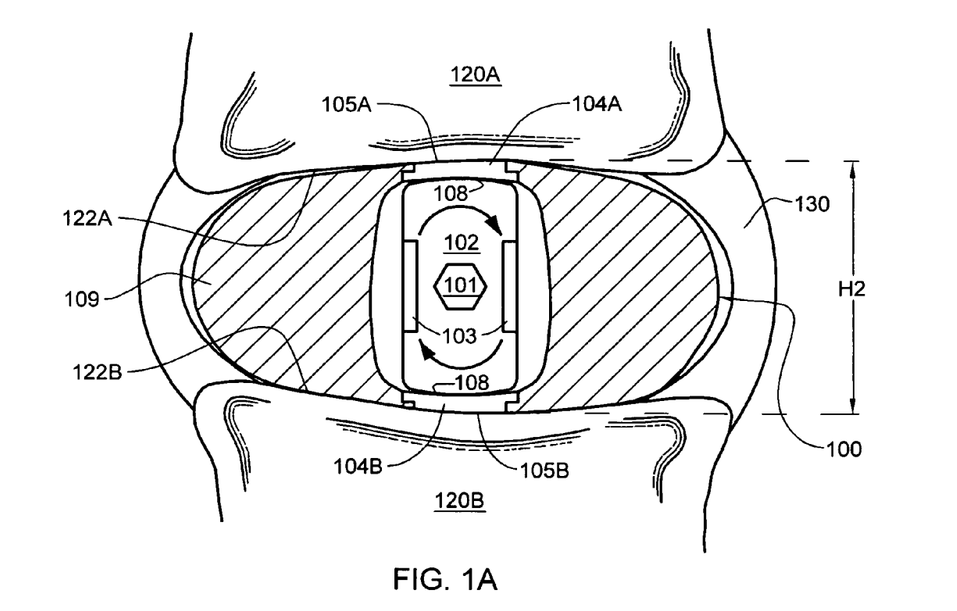
FIG. 1A depicts the nucleus replacement implant of FIG. 1, showing the nucleus replacement implant in an extended height configuration within the intervertebral disc nucleus space, in accordance with an aspect of the present invention.

Referring now to FIGS. 1 & 1A, one embodiment of a nucleus replacement implant 100 is illustrated, in accordance with aspects of the present invention. Implant 100 is shown positioned within an intervertebral disc nucleus space 110 defined by superior and inferior vertebral members 120A, 120B, respectively, and an annulus fibrosis 130.

As shown, nucleus replacement implant 100 includes a centrally-disposed, core support structure comprising a rotatable member 102 and two vertebral (plate-shaped) support structures 104A, 104B. The core support structure, which may be fabricated of metal, a non-elastic biocompatible material, or an elastic polymer (of higher stiffness than the elastic body), is shown in FIG. 1 with rotatable member 102 in a first, horizontal orientation, resulting in the implant 100 being in a compressed height configuration of height H1. In FIG. 1A, rotatable member 102 is shown rotated to a second, vertical orientation, resulting in implant 100 being in an extended height configuration of height H2, wherein H2>H1, with vertebral support structures 104A, 104B forced into physical contact with respective vertebral endplates of 122A, 122B of the vertebral members 120A, 120B. More particularly, outer contact surfaces 105A, 105B of the vertebral support structures 104A, 104B are forced into physical contact with the respective vertebral endplates 122A, 122B, thereby conforming the core support structure to the shape of the vertebral endplates. Additionally, the at least two vertebral support structures 104A, 104B each includes a slightly concave, inwardly-facing contact surface 107A, 107B designed to engage one of the slightly convex ends 108 of rotatable member 102. The slightly concave and convex opposing surfaces 107A, 107B, 108 facilitate securing or retaining the core support structure in the load bearing configuration illustrated in FIG. 1A when the rotatable member is positioned in the second orientation, and the implant is in the extended height configuration.

Referring more particularly to rotatable member 102, in this embodiment, the member is shown to comprise a barrel-shaped member with rounded corners to facilitate rotation of the member between the first and second orientations. In practice, the rotatable member could comprise any rotatable member capable of functioning as described herein, including a barrel-shaped member, a cam-shaped member, a cylindrical-shaped member, an elliptical-shaped member, a rectangular-shaped member, a tubular-shaped member, etc. In the example shown, rotatable member 102 has a first width W1 in a first dimension and a second width W2 in a second dimension, wherein W2>W1. The size difference between width W1 and width W2 directly relates to the difference in heights H2, H1 between the extended height configuration and the compressed height configuration of the implant.

In this embodiment, rotatable member 102 further includes a center-disposed opening 101 configured for facilitating rotating of the rotatable member. As shown, the center opening 101 in this example is a hexagonal-shaped opening. However, those skilled in the art will note that the opening could comprise any desired shape, including a rectangular shape, a square shape, a cross shape, etc. Further, those skilled in the art will note that rotation of the rotatable member 102 assumes the existence of an instrument or tool (not shown) having an end with a corresponding male configuration for mating with the opening 101 in the rotatable member. This example further includes rectangular-shaped openings or slots 103 disposed along different edge surfaces of the rotatable member. These openings 103 further facilitate manipulation of the rotatable member 102, e.g., through the use of an appropriately configured fork-type instrument (not shown) having tines sized to engage the rectangular openings 103.

At least partially surrounding the core support structure is an elastic body 109 which comprises a biocompatible material, such as a PurSil polymer offered by the Polymer Technology Group of Emeryville, Calif. The central core structure and elastic body are sized to substantially fill the disc cavity when in the extended height configuration of FIG. 1A. The dimensions of the load bearing, core support structure, including rotatable member 102 and vertebral support structures 104A, 104B, may vary depending upon the particular sized cavity within which the implant is to be inserted, but are fabricated to facilitate introduction of the implant in a collapsed configuration into an intervertebral disc space. When in the operational, extended height configuration, the core support structure of the implant is wide enough to support the adjacent vertebrae and is of a height sufficient to appropriately separate the vertebrae. In order to provide long term mechanical support to the intervertebral disc, the volume of the implant in the disc space should be 80% to 90% or more of the volume of the entire disc space. By way of example only, an implant might have a height H2 in the range of 8-14 mm.

The biocompatible material employed in the elastic body is referred to herein as "disc nucleus material" or "nucleus replacement material" since they are used as such, even though the material may not come from a disc nucleus. Accordingly, the elastic body is described herein as formed of a disc nucleus material or a nucleus replacement material, which is any material to be used to augment, repair or replace all or a portion of the intervertebral disc nucleus, regardless of the source of that material.

It is to be appreciated that the inventive method described above finds particular utility with materials described in U.S. patent application Ser. No. 10/645,006 (Patent Application Publication No. US 2005/0043801 A1), and in U.S. patent application Ser. No. 10/426,613 (Patent Application Publication No. US 2004/0220631 A1). Both of those applications disclose materials that may be dehydrated prior to implantation, and are then rehydrated to a larger size after implantation. The inventive methods described above also find particular utility with materials described in the above-incorporated U.S. patent application Ser. No. 09/943,441 (Patent Application Publication No. US 2002/0026244 A1), which discloses implants having a shape memory that allows the implant to be manipulated to a configuration having a smaller cross-section before implantation, and then relaxed to a configuration having a larger cross-section after implantation.

To position the implant in an intervertebral disc nucleus space, a small incision (e.g., hole) is first cut in the annulus of the disc being repaired or augmented. A guide wire or other small instrument may be used to make the initial hole. If necessary, successively larger holes are cut from an initially small puncture. The purpose of the hole (also called an aperture, an opening, or a portal, for example) is to allow passage of the implant in the compressed height configuration into the disc nucleus space from the side (i.e., through the annulus). It is preferred, though, for the hole to be as small as possible to minimize expulsion of the implant through the hole after the surgery is complete.

Once a small hole is provided, a dilating instrument may be employed to stretch the hole temporarily, while avoiding tearing, so that the hole can return back to its un-dilated size after the nucleus replacement implant has been positioned within the intervertebral disc nucleus space. Even if some tearing or permanent stretching occurs, the dilation is preferably accomplished in a manner that allows the hole to return to a size smaller than its dilated size after the surgery is complete.

After the nucleus replacement implant has been delivered into the disc nucleus space, the rotatable member is rotated to the second orientation so that the nucleus replacement implant is in the extended height configuration. Preferably, the hole in the annulus is smaller than the nucleus replacement implant when in the extended height configuration, thereby inhibiting expulsion of the implant from the disc nucleus space. Thus, if the annulus has been stretched or torn so that it does not return to its original size, it should at least be to a size smaller than the implant in the extended height configuration.

In one embodiment, the method described above is used to deliver an implant that has two configurations—a first configuration and a second configuration—wherein one of the configurations presents a cross-section that is smaller than the other configuration. With this embodiment, it is possible to implant the device through the dilated annular opening when the implant is in its smaller (e.g., compressed and elongated) configuration, and then cause the implant to assume its larger (e.g., extended height) configuration after it has been passed through the inserter positioned in the dilated hole in the annulus.

As to the specifics of the method used to deliver the "two configuration" implants, the basic principles of cutting a small hole in the disc annulus and dilating the annulus enough to allow the disc nucleus device to pass through the hole apply. In this embodiment though, when the instrument is withdrawn the implant is caused to assume a shape and/or size larger than the shape/size that was presented when the device was implanted. For example, after implantation, the rotatable member is rotated from the first orientation to the second orientation, thereby placing the nucleus replacement implant in the extended height configuration of height H2. Further, when a dehydrated material is used as the elastic body, the material is allowed to swell up in the disc space so that the rehydrated material is larger than the dehydrated material. Then, when the instrument is withdrawn and the hole in the annulus returns to a smaller size, the disc nucleus implant finds it even more difficult to fit back through the hole. This further mitigates the need for an annular plug or sutures to prevent expulsion of the disc nucleus material.

As to other possible disc nucleus implant configurations, a spinal disc implant could comprise a biomechanical or otherwise flexible material to facilitate its conversion from an inserting configuration to a support configuration. Further, the spinal disc implant may include a load bearing structure surrounded by an outer, resorbable or otherwise temporary, shell. The outer shell advantageously anchors the core support structure within the intervertebral disc space. The surface of the implant may include various surface features, including various macro-surface patterns, and chemical or physical modifications to further enhance fixation of the implant. The surface features, such as the macro-surface patterns and physical modifications, for example, may enhance fixation of the elastic body to surrounding tissue.

The dimensions of the spinal disc implants used herein may vary depending on the particular case, but the implant is typically configured and sized for introduction into an intervertebral disc nucleus space. Moreover, the core support structure of the implant is preferably wide enough to support adjacent vertebrae and is of height sufficient to separate the adjacent vertebrae.

The spinal disc implants used in the invention may be fabricated in a wide variety of shapes, as desired for a particular application. Although the implant may assume a variety of shapes, it is typically shaped to conform to the shape of the natural nucleus pulposus, at least when in its hydrated and/or relaxed configuration. Thus, the implants may be substantially elliptical when in their hydrated and/or relaxed configurations. In other forms of the invention, the shape of the implants in their hydrated and/or relaxed configurations may be generally annular-shaped, cylindrical-shaped, or otherwise shaped as required to conform to the intervertebral disc cavity.

The spinal disc implants are also shaped in a manner to allow easy implantation into a spinal disc nucleus space. The elastic body of a spinal disc implant for use in the invention may be formed from a wide variety of biocompatible polymeric materials, including elastic materials, such as elastomeric materials, hydrogels or other hydrophilic polymers, or composites thereof. Suitable elastomers include silicone, polyurethane, copolymers of silicone and polyurethane, polyolefins, such as polyisobutylene and polyisoprene, neoprene, nitrile, vulcanized rubber and combinations thereof. The vulcanized rubber described herein may be produced, for example, by a vulcanization process utilizing a copolymer produced as described, for example, in U.S. Pat. No. 5,245,098 to Summers et al. from 1-hexene and 5-methyl-1,4-hexadiene. Suitable hydrogels include natural hydrogels, and those formed from polyvinyl alcohol, acrylamides such as polyacrylic acid and poly(acrylonitrile-acrylic acid), polyurethanes, polyethylene glycol, poly(N-vinyl-2-pyrrolidone), acrylates such as poly(2-hydroxy ethyl methacrylate) and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include naturally occurring materials such as glucomannan gel, hyaluronic acid, polysaccharides, such as cross-linked carboxyl-containing polysaccharides, and combinations thereof. The nature of the materials employed to form the elastic body can be selected so the formed implants have sufficient load bearing capacity. In certain embodiments, a compressive strength of at least about 0.1 Mpa is desired, although compressive strengths in the range of about 1 Mpa to about 20 Mpa may also be preferred.

When the body of the implant is formed from an elastic material, such as hydrogel, or other similar hydrophilic material, or include a resorbable outer shell, the body may advantageously deliver desired pharmacological agents. The pharmacological agent may be a growth factor that may advantageously repair the endplates and/or the annulus fibrosis. For example, the growth factor may include an osteoinductive factor (e.g., a bone morphogenetic protein), transforming growth factor-ss (TGF-ss), insulin-like growth factor, platelet derived growth factor, fibroblast growth factor or other similar growth factor or combination thereof having the ability to repair the endplates and/or the annulus fibrosis of an intervertebral disc. In one embodiment, the spinal disc implant comprises an osteoinductive factor.

Osteoinductive factors can be defined as those factors, which stimulate uncommitted cells, e.g., mesenchymal stem cells, to convert phenotypically to chondroprogenitor and osteoprogenitor cells. Osteogenic factors include those factors that contain cells that are committed to osteoblastic phenotypes or stimulate committed osteoprogenitor cells and mature osteoblasts to proliferate. Thus, the major distinction between the two factors is that cellular proliferation characterizes an osteogenic factor, whereas cellular differentiation characterizes an osteoinductive factor. It will be understood that an osteoinductive factor and an osteogenic factor can be contained in a spinal disc implant either alone, or in combination, providing for a synergistic effect.

Suitable osteoinductive factors for use in the invention include growth factors to stimulate or induce bone growth, including factors comprised of protein or genes. Recombinant human bone morphogenetic proteins (rhBMPs) are preferred. More particularly, the bone morphogenetic protein may be a rhBNMP-2, rhBMP-4 or heterodimers thereof. Bone morphogenic protein (BMP), an osteoinductive cytokine extracted from bone matrix, is capable of inducing bone formation when implanted in a fracture of surgical bone site. BMP actually refers to a group of bone morphogenetic proteins belonging to the TGF-β superfamily. The structures of eleven proteins, BMP-1 through BMP-13 have been elucidated. Recombinantly produced human bone morphogenic protein-2 has been demonstrated in several animal models to be effective in regenerating bone in skeletal defects.

Recombinant BMP-2 can be used at a concentration of about 0.4 mg/ml to about 4.0 mg/ml, preferably about 1.0 to 3.0 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described in U.S. Pat. No. 4,294,753 to Urist, and Urist et al., 81 PNAS 371, 1984.

In other forms of the invention, the spinal disc implants may comprise a pharmacological agent used for treating various spinal conditions, including degenerative disc disease, spinal arthritis, spinal infection, spinal tumor and osteoporosis.

Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents are preferably dispersed within the hydrogel, or other hydrophilic, implant for in vivo release, and/or, with respect to the implants with the resorbable other shell, may be dispersed in the outer shell. The hydrogel can be cross-linked chemically, physically, or by a combination thereof, in order to achieve the appropriate level of porosity to release the pharmacological agents at a desired rate. The agents may be released upon cyclic loading, and, in the case of implants including a resorbable outer shell, upon resorption of the shell.

The pharmacological agents may be dispersed in the implants by adding the agents to the solution used to form the implant, by soaking the formed body of the implant in an appropriate solution containing the agent, or by other appropriate methods known to the skilled artisan. In other forms of the invention, the pharmacological agents may be chemically or otherwise associated with the implant. For example, the agents may be chemically attached to the outer surface of the body of the implant.

Referring further to the drawings, and as noted briefly above, FIGS. 2 & 2A, 3 & 3A and 4 & 4A each depict alternate embodiments of a disc nucleus implant, in accordance with aspects of the present invention. Unless otherwise stated, each disc nucleus implant is assumed to be constructed and to function in a manner similar to that described above in connection with the embodiment of FIGS. 1 & 1A.

Figure 2:
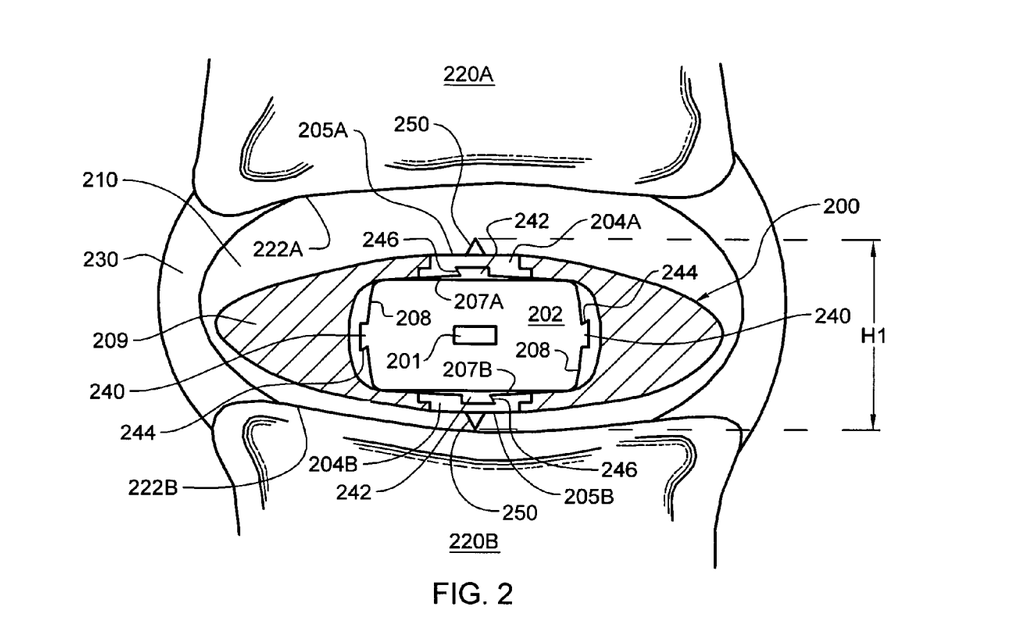
FIG. 2 is a cross-sectional, side elevational view of another embodiment of a nucleus replacement implant in compressed height configuration disposed within an intervertebral disc nucleus space, in accordance with an aspect of the present invention.
Figure 2A:
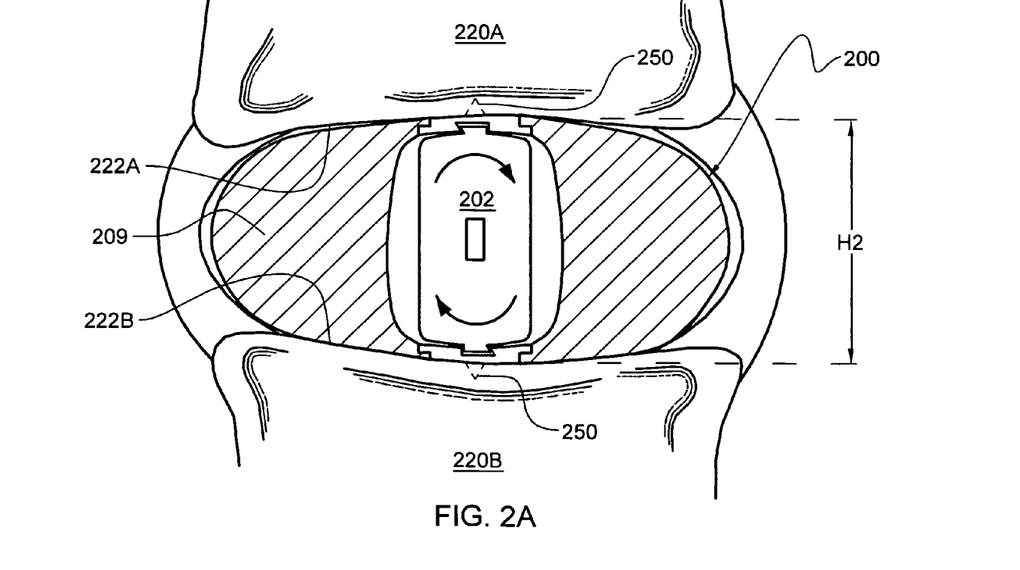
FIG. 2A depicts the nucleus replacement implant of FIG. 2, showing the implant in an extended height configuration within the intervertebral disc nucleus space, in accordance with an aspect of the present invention.

Referring to FIGS. 2 & 2A, a nucleus replacement implant 200 is shown, again disposed within an intervertebral disc nucleus space 210, defined between superior and inferior vertebral members 220A, 220B, respectively, and an annulus fibrosis 230.

In this embodiment, implant 200 includes a rotatable member 202 and at least two vertebral (plate-shaped) support structures 204A, 204B. In FIG. 2, the core support structure is shown with rotatable member 202 in a first, horizontal orientation, resulting in the implant being in a compressed height configuration of height H1, while in FIG. 2A, the rotatable member 202 is shown rotated to second, vertical orientation, resulting in the implant being in an extended height configuration of height H2 (wherein H2>H1), with vertebral support structures 204A, 204B forced into physical contact with the respective vertebral endplates 222A, 222B of vertebral bodies 220A, 220B. As described above, the core support structure is surrounded by an elastic body 209, e.g., comprising a preformed biocompatible material. The core support structure and the elastic body of implant 200 may comprise materials and configurations such as those described above in connection with the implant 100 embodiment of FIGS. 1 & 1A.

In this embodiment, a single, central opening 201 is provided in rotatable member 202. As shown, opening 201 is a rectangular-shaped opening (by way of example), which with insertion of an appropriately configured rectangular-shaped tool, allows for rotation of the rotatable member 202 between the first orientation and the second orientation.

Further, in this embodiment, the rotatable member includes latching members 240 projecting from end surfaces 208. These latching members 240 are sized and shaped to mate with respective latching recesses 242 in the inwardly-facing surfaces 207A, 207B of the vertebral support structures 204A, 204B, respectively. In the embodiment shown, latching members 240 each includes a rake-angled edge 244, which is configured to mate with a rake-angled surface 246 in the latching recesses 242 of the vertebral support structures to further assist in locking the rotatable member in the second, vertical orientation.

As a further variation, implant 200 includes structures 250 projecting from the outer contact surfaces 205A, 205B of the vertebral support structures 204A, 204B. These outwardly projecting structures (for example, spikes) are designed to assist in anchoring the implant in place within the intervertebral disc nucleus space once the implant is in the extended height configuration illustrated in FIG. 2A. That is, the projecting structures 250 are designed to penetrate the vertebral endplates 222A 222B, and thereby anchor the implant 200 in a fixed position within the disc cavity 210.

Figure 3:
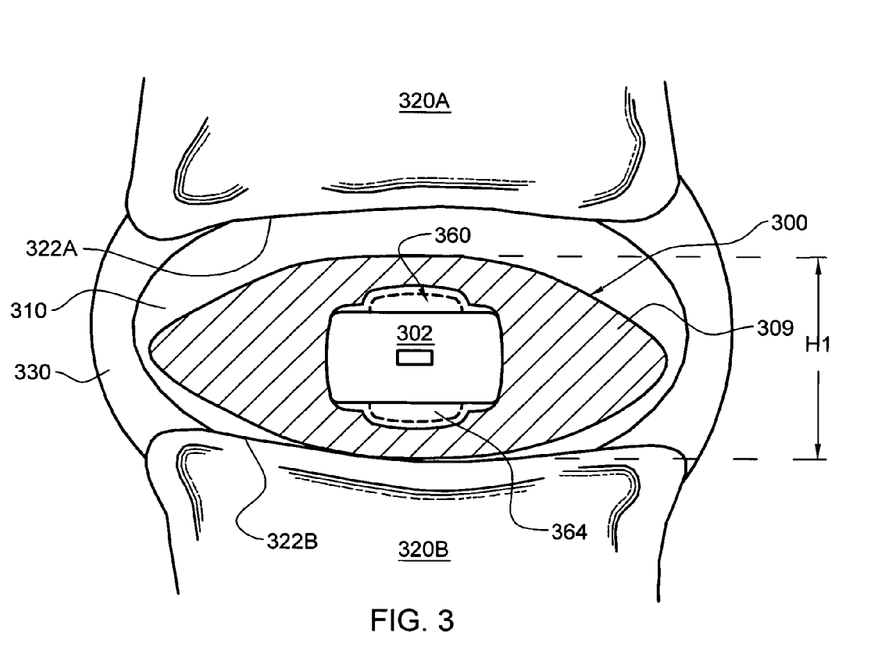
FIG. 3 is a cross-sectional, side elevational view of still another embodiment of a nucleus replacement implant in compressed height configuration disposed within an intervertebral disc nucleus space, in accordance with an aspect of the present invention.
Figure 3A:
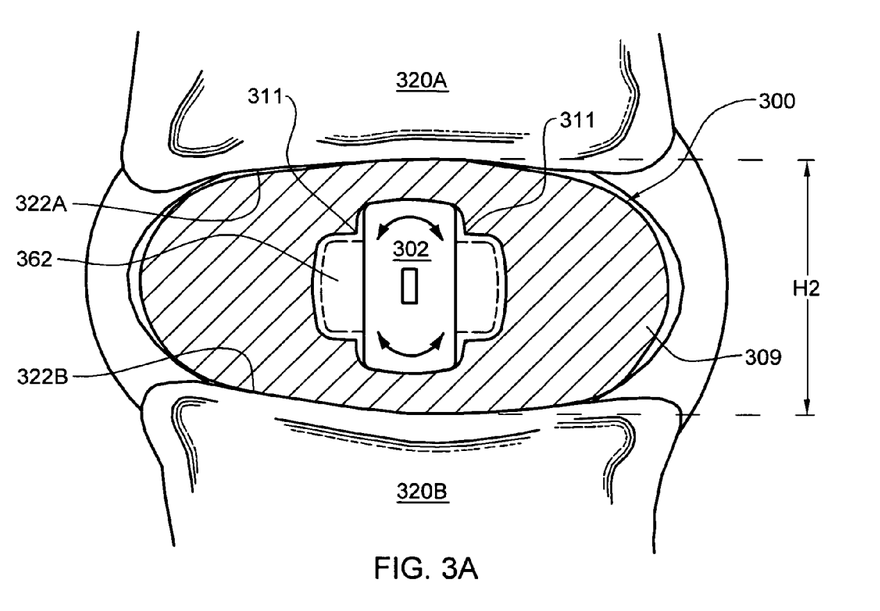
FIG. 3A depicts the nucleus replacement implant of FIG. 3, showing the implant in an extended height configuration within the intervertebral disc nucleus space, in accordance with an aspect of the present invention.

FIGS. 3 & 3A depict a further embodiment of an implant 300, in accordance with aspects of the present invention. In this embodiment, the central core structure comprises a rotatable member 302, which is at least partially surrounded by a preformed elastic body 309. Implant 300 is shown in an intervertebral disc nucleus space 310 defined between superior and inferior vertebral members 320A, 320B, respectively, and an annulus fibrosis 330. The core support structure is shown with the rotatable member 302 in a first, horizontal orientation in FIG. 3, resulting in the implant being in a compressed height configuration of height H1. In FIG. 3A, rotatable member 302 of the core support structure is shown rotated to a second, vertical orientation, resulting in the implant being in an extended height configuration of height H2 (wherein H2>H1), with exterior surfaces of elastic body 309 forced into physical contact with the respective vertebral endplates 322A, 322B of vertebral members 320A, 320B. Again, unless otherwise illustrated and described, the core support structure and the elastic body of implant 300 may comprise materials and configurations similar to those described above in connection with the implant 100 embodiment of FIGS. 1 & 1A.

As shown, rotatable member 302 resides within a centrally-disposed chamber 360 formed in the elastic body 309. This centrally-disposed chamber includes intersecting horizontally-disposed and vertically-disposed chambers 362, 364. Rotatable member 302 is in the first orientation (FIG. 3) when positioned within the horizontally-disposed chamber 362, and is in the second orientation (FIG. 3A) when positioned within the vertically-disposed chamber 364. Elastic body 309 includes inward projections 311, which serve to partially define and separate the intersecting horizontally-disposed and vertically-disposed chambers. These inward projections 311 further assist in maintaining rotatable member 302 in one of the first orientation and the second orientation.

Figure 4:
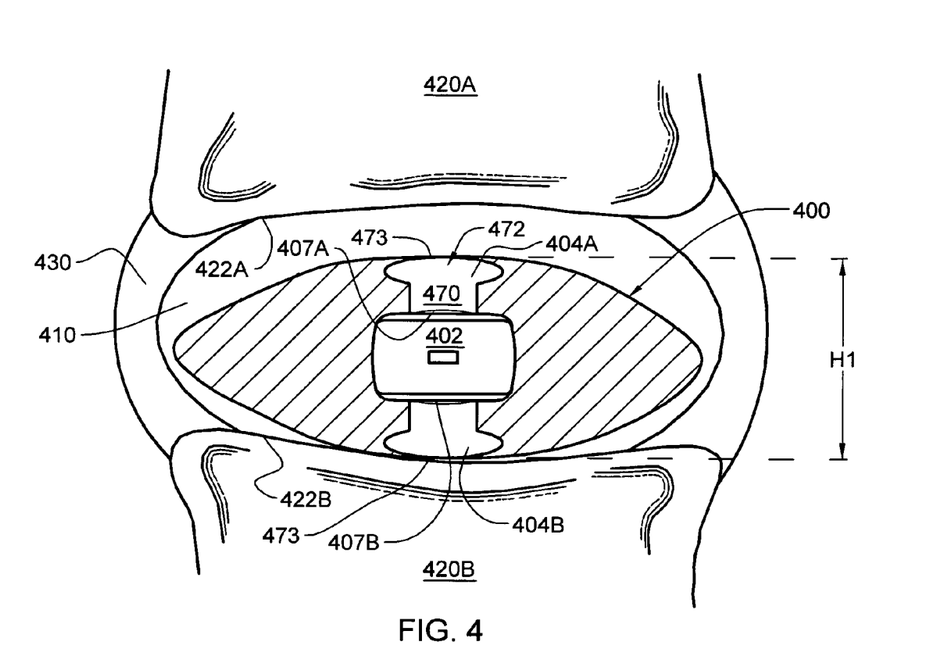
FIG. 4 is a cross-sectional, side elevational view of a further embodiment of a nucleus replacement implant in compressed height configuration disposed within an intervertebral disc nucleus space, in accordance with an aspect of the present invention.
Figure 4A:
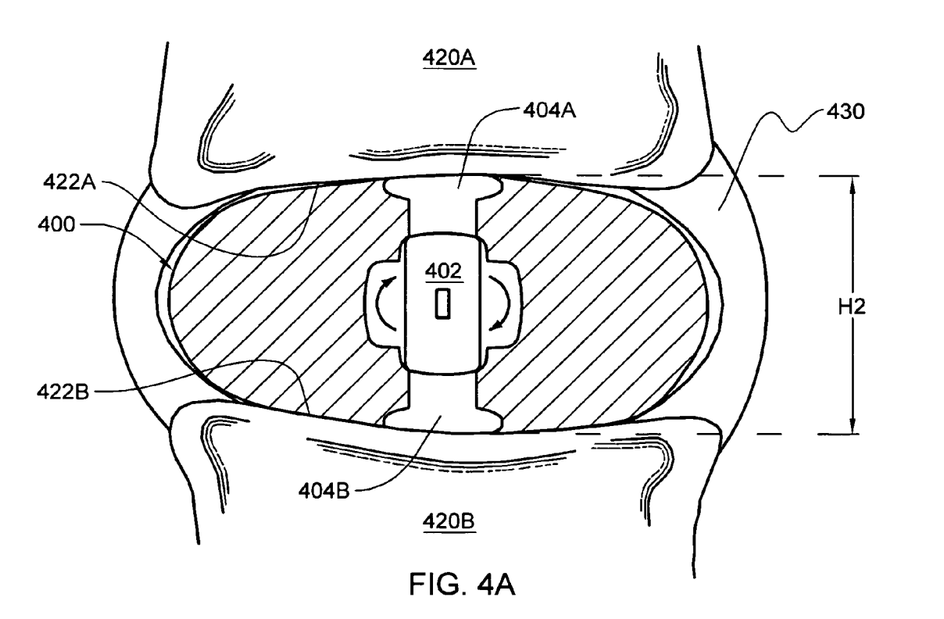
FIG. 4A depicts the nucleus replacement implant of FIG. 4, showing the implant in an extended height configuration within the intervertebral disc nucleus space, in accordance with an aspect of the present invention.

FIGS. 4 & 4A depict a further embodiment of an implant 400, shown in an intervertebral disc nucleus space 410 defined between superior and inferior vertebral members 420A, 420B and an annulus fibrosis 430. In this embodiment, implant 400 includes a centrally-disposed, core support structure comprising a rotatable member 402 and multiple vertebral (mushroom-shaped) support structures 404A, 404B. The core support structure is shown with the rotatable member 402 in a first, horizontal orientation in FIG. 4, resulting in the implant being in a compressed height configuration of height H1, and in a second, vertical orientation in FIG. 4A, resulting in the implant being in an extended height configuration of height H2 (wherein H2>H1), with the vertebral support structures 404A, 404B forced in physical contact with the respective vertebral endplates 422A, 422B of vertebral members 420A, 420B. Again, unless otherwise illustrated and described, the core support structure and the elastic body of implant 400 may comprise materials and configurations similar to those described above in connection with the implant 100 embodiment of FIGS. 1 & 1A.

As noted, in this embodiment, vertebral support structures 404A, 404B are each a mushroom-shaped structure comprising a center post or column 470 with an enlarged, roughly spherical, cap 472 extending therefrom. Outer contact surface 473 of each cap 472 is configured to mate with a respective vertebral endplate 422A, 422B when the implant is in the extended height configuration illustrated in FIG. 4A. The inwardly-facing surfaces 407A, 407B of vertebral support structures 404A, 404B are slightly concave similar to that noted above with reference to the implant embodiment of FIGS. 1 & 1A.

At least partially surrounding the core support structure is an elastic body 409, e.g., comprising a preformed, biocompatible material. Again, the elastic body is sized to substantially fill the disc cavity when the implant is in the extended height configuration of FIG. 4A. The dimensions of the load bearing, core support structure, including rotatable member 402 and vertebral support structures 404A, 404B, may vary depending upon the particular size cavity within which the implant is to be inserted. As with the other embodiments, these structures are fabricated to facilitate introduction of the implant in a collapsed configuration into the intervertebral disc space, and to then be extended, by rotation of the rotatable member, to a height H2 selected to provide sufficient support and spacing to the adjacent vertebrae.

EXAMPLE

A medical patient may be treated to replace a damaged or degenerated lumbar intervertebral disc nucleus using the procedure described above.

A/P and M/L radiographs are obtained to determine the size and shape of the affected level. The largest implant that can be accommodated by patient anatomy without overdistraction is selected, choosing (for example) among implants having footprints of 19 mm×23 mm to 22 mm×27 mm, and a height of between 6 mm and 14 mm. It is important to select the tallest device that can be accommodated by the interbody space. Excessive annulus laxity may cause non-central seating of the implant. X-ray templates are used to determine whether a small or large device footprint should be used, as are AP and ML implant outlines to determine the appropriate height.

The patient is placed in a direct prone position on the operating table, bolstered appropriately to maintain lumbar lordosis. C-arm fluoroscopy is not absolutely necessary for the procedure, but is preferred if available. Intraoperative imaging is useful for evaluation of the nucleus cavity preparation, as well as for adjusting and confirming device orientation.

A 5 cm incision is made in the midline directly over the posterior spinous processes. The skin incision is sharply carried down through the subcutaneous tissues to the dorsal lumbar fascia. Great care is taken to preserve the midline ligamentous structures. A longitudinal incision is made in the dorsal lumbar fascia 5 mm lateral to the posterior spinous processes. The multifidus is subperiostally elevated off the posterior spinous processes and adjacent lamina. Great care is taken to protect and preserve the facet joint capsule and joint.

A high speed burr is used to create a small laminotomy window. The ligaments flavum is sharply incised and removed. A Kerrison rongeur is used to enlarge the laminotomy site if necessary. The traversing nerve root is identified and gently retracted medially.

Epidural veins are coagulated using bipolar electrocautery. The posterior annulus is identified. A working portal through the annulus is created following insertion of the trephine device.

Preservation of the annulus fibrosis minimizes the risk of implant expulsion. A progressive dilation technique is employed to gain access to the nucleus pulposus. If properly dilated and protected, the viscoelastic annulus fibers should relax postoperatively, leaving only a small defect.

A starting hole is created in the annulus using a 3 mm trephine. The first dilator is then inserted, taking care not to damage the anterior margin of the annulus. Larger dilators are then provided over each shaft in sequence until the desired access is achieved.

A variety of tools are used to properly clear the nucleus cavity, including specialized pituitary rongeurs and curettes for reaching the contralateral margin of the nucleus pulposus. Ring curettes are used to scrape adhesions from the vertebral endplates if necessary. Care is taken to thoroughly prepare the cavity such that it is centralized, symmetrical, and large enough to accept the desired implant footprint. Care is also taken to avoid damaging the annulus fibrosis.

The endplate jack is inserted into the intervertebral space and is actuated until moderate distraction is achieved. Care is taken to avoid overdistraction. The position is maintained for approximately 60 seconds to allow the annulus fibers to relax, adjusting if necessary during the process. The height on the jack scale is identified and the corresponding implant is selected. When the desired implant falls between sizes, the smaller implant size is selected.

An instrument set containing numerous device inserter bodies, with internal geometry specific to corresponding implants, can be used to insert the implant. All inserter bodies can interface with a common ratchet assembly and pusher rod, as described in various ones of the above-incorporated patents and applications. The inserter body is chosen to correspond to the correct implant size and the implant is loaded into the instrument.

The inserter functions much like a caulking gun. The loaded inserter body is assembled with the ratchet handle, and the pusher rod is positioned into the ratchet handle until it touches the nucleus replacement device. The ratchet handle assembly is then actuated to advance the implant to a position just before the inserter exit. This minimizes the time and travel required for insertion of the device once the instrument is installed at the operative site.

The inserter tip is placed in the annular opening prior to extruding the nucleus replacement device. As the nucleus replacement device fills the nucleus cavity, it may tend to push the inserter out of the disc space. Moderate axial force may be applied during the final stage of extrusion to counter this effect.

Further, using fluoroscopic control, the final position of the nucleus replacement material can be adjusted using a tamp. Positioning can be verified by inspection of radiographic markers embedded in the implant. For example, an anterior marker can be provided slightly larger than two posterior markers. If ideally placed, three collinear markers are visible in the frontal plane, with the central marker being larger than the outer two. In the sagittal plane, a larger anterior marker and two closely positioned posterior marker are visible. This ideal placement may not be necessary because the implant will float and rotate slightly as it finds a natural center in the nucleus space.

Once the nucleus replacement implant is correctly positioned in the intervertebral disc nucleus space (in the compressed height configuration), the rotatable member is rotated to the second orientation so that the nucleus replacement implant assumes the extended height configuration, with the core support structure forced into physical contact with the respective vertebral endplates, thereby separating the endplates and providing the desired disc support.

Although preferred embodiments are depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An intervertebral disc nucleus replacement implant configured to reside within an intervertebral disc nucleus space, the implant comprising:
    a centrally disposed, core support structure comprising a solid, rotatable member, the rotatable member being rotatable between a first orientation and a second orientation;
    an elastic body formed separate from the centrally disposed, core support structure and comprising a centrally-disposed chamber with a center position, the rotatable member being disposed within the centrally-disposed chamber of the elastic body and intersecting the center position thereof, wherein the elastic body comprises a biocompatible material at least partially surrounding and engaging the core support structure, the elastic body being sized and configured to at least partially, permanently fill and conform to the intervertebral disc nucleus space when the implant is in operative position therein; and
    wherein when the rotatable member is in the first orientation, the elastic body is collapsed in a collapsed height configuration of height H1 to facilitate insertion of the nucleus replacement implant into the intervertebral disc nucleus space, and when the rotatable member is in the second orientation, the elastic body is expanded in an operative, extended height configuration of height H2, wherein H2>H1, to facilitate use of the nucleus replacement implant as a prosthetic intervertebral disc nucleus replacement, and wherein the rotatable member rotates between the first orientation and the second orientation without rotating the elastic body.

2. The nucleus replacement implant of claim 1, wherein the rotatable member has a first width W1 in a first dimension and a second width W2 in a second dimension, wherein W2>W1, and wherein when the nucleus replacement implant is disposed within the intervertebral disc nucleus space and the rotatable member is in the first orientation, width W1 of the rotatable member is oriented substantially vertical within the intervertebral disc nucleus space, and when in the second orientation, width W2 of the rotatable member is oriented substantially vertical.

3. The nucleus replacement implant of claim 1, wherein the rotatable member comprises one of: a barrel-shaped member, a cam-shaped member, a cylindrical-shaped member, an elliptical-shaped member, a rectangular-shaped member, or a tubular-shaped member.

4. The nucleus replacement implant of claim 1, wherein the rotatable member is fabricated of metal, a non-elastic biocompatible material or an elastic polymer of higher stiffness than the surrounding elastic body.

5. The nucleus replacement implant of claim 1, wherein the rotatable member includes at least one opening configured for facilitating rotating of the rotatable member.

6. The nucleus replacement implant of claim 5, wherein the at least one opening comprises at least one center opening in a center portion of the rotatable member.

7. The nucleus replacement implant of claim 6, wherein the at least one center opening in the center portion of the rotatable member comprises at least one of a hexagonal-shaped opening or a rectangular-shaped opening.

8. The nucleus replacement implant of claim 5, wherein the at least one opening comprises a rectangular-shaped slot formed in a center portion of the rotatable member.

9. The nucleus replacement implant of claim 6, wherein the rotatable member includes multiple rectangular-shaped slots, at least two rectangular-shaped slots being disposed along respective edge surfaces of the rotatable member to facilitate manipulation of the rotatable member.

10. The nucleus replacement implant of claim 1, wherein the rotatable member resides within a centrally-disposed chamber in the elastic body.

11. An intervertebral disc nucleus replacement implant configured to reside within an intervertebral disc nucleus space, the implant comprising:
a centrally disposed, core support structure comprising a solid, rotatable member, the rotatable member being rotatable between a first orientation and a second orientation;
an elastic body comprising biocompatible material at least partially surrounding and engaging the core support structure, the elastic body being sized and configured to at least partially, permanently fill the intervertebral disc nucleus space when the implant is in operative position therein;
wherein when the rotatable member is in the first orientation, the nucleus replacement implant is in a compressed height configuration of height H1 to facilitate insertion of the nucleus replacement implant into the intervertebral disc nucleus space, and when the rotatable member is in the second orientation, the nucleus replacement implant is in an operative, extended height configuration of height H2, wherein H2>H1, to facilitate use of the nucleus replacement implant as a prosthetic intervertebral disc nucleus replacement;
wherein the rotatable member resides within a centrally-disposed chamber in the elastic body; and
wherein the centrally-disposed chamber is cross-shaped and comprises intersecting horizontally oriented and vertically oriented chambers, wherein the rotatable member is in the first orientation when positioned within the horizontally oriented chamber, and is in the second orientation when positioned within the vertically oriented chamber, and wherein an inner wall of the elastic body defines the cross-shaped, centrally disposed chamber comprising the horizontally oriented chamber and vertically oriented chamber, and comprises inward projections which assist in maintaining the rotatable member in one of the first orientation and the second orientation.

12. An intervertebral disc nucleus replacement implant configured to reside within an intervertebral disc nucleus space, the implant comprising:
a core support structure comprising:
a centrally disposed, rotatable member, the rotatable member being rotatable between a first orientation and a second orientation;
at least two solid, vertebral support structures in spaced relation, with the rotatable member being disposed therebetween;
an elastic body formed separate from the core support structure and comprising biocompatible material at least partially surrounding the core support structure and coupled to the at least two vertebral support structures, the elastic body being sized and configured to at least partially, permanently fill and conform to the intervertebral disc nucleus space when the implant is in operative position therein; and
wherein the rotatable member resides within a centrally disposed chamber in the elastic body; and
wherein when the rotatable member is in the first orientation, the elastic body is collapsed in a collapsed height configuration of height H1 to facilitate insertion of the nucleus replacement implant into the intervertebral disc nucleus space, and when the rotatable member is in the second orientation, the elastic body is expanded in an operative, extended height configuration of height H2, wherein H2>H1, to facilitate use of the nucleus replacement implant as a prosthetic intervertebral disc nucleus replacement, and wherein the rotatable member rotates between the first orientation and the second orientation without rotating the elastic body.

13. The nucleus replacement implant of claim 12, wherein the at least two vertebral support structures of the core support structure comprise two support plates, each support plate being disposed at a respective apex of the nucleus replacement implant, the apexes being defined with the rotatable member in the second orientation and the implant in the extended height configuration of height H2, and wherein when the nucleus replacement implant is disposed within the intervertebral disc nucleus space and the rotatable member is in the second orientation, each support plate is sized and configured to contact a vertebral endplate of a respective vertebral member partially defining the intervertebral disc nucleus space, and wherein the core support structure physically supports the two vertebral endplates in spaced relation.

14. The nucleus replacement implant of claim 12, wherein the rotatable member has a first width W1 in a first dimension and a second width W2 in a second dimension, wherein W2>W1, and wherein when the nucleus replacement implant is disposed within the intervertebral disc nucleus space and the rotatable member is in the first orientation, width W1 of the rotatable member is oriented substantially vertical within the intervertebral disc nucleus space, and when in the second orientation, width W2 of the rotatable member is oriented substantially vertical.

15. The nucleus replacement implant of claim 12, wherein the rotatable member comprises one of: a barrel-shaped member, a cam-shaped member, a cylindrical-shaped member, an elliptical-shaped member, a rectangular-shaped member, or a tubular-shaped member.

16. The nucleus replacement implant of claim 12, wherein the rotatable member and the two vertebral support structures are each fabricated of metal, a non-elastic biocompatible material or an elastic polymer of higher stiffness than the surrounding elastic body.

17. The nucleus replacement implant of claim 12, wherein the rotatable member includes at least one opening configured for facilitating rotating of the rotatable member.

18. The nucleus replacement implant of claim 12, wherein the at least two vertebral support structures each includes an inwardly-facing, concave surface configured for mating with a respective convex end surface of the rotatable member when the rotatable member is in the second orientation, the respective mating of the concave and convex surfaces assisting in maintaining the rotatable member in the second orientation.

19. The nucleus replacement implant of claim 18, wherein the vertebral support structures are each configured as one of a mushroom-shaped support structure or a plate-shaped support structure having a side surface coupled to the elastic body.

20. The nucleus replacement implant of claim 12, wherein the rotatable member includes two end surfaces, the two end surfaces each physically contacting a respective inwardly-facing surface of a different one of the vertebral support structures when the rotatable member is in the second orientation, and wherein the end surfaces of the rotatable member each includes a latching element extending therefrom, and wherein the inwardly-facing surfaces of the vertebral support structures each includes a correspondingly configured latching recess to allow latching of the rotatable member relative to the vertebral support structures when the rotatable member is in the second orientation with the latching elements thereof disposed within the latching recesses of the vertebral support structures.

21. The nucleus replacement implant of claim 20, wherein each latching element of the rotatable member includes a rake-angled edge, and wherein each latching recess of the vertebral support structures includes a corresponding rake-angled surface, wherein the rake-angled edges and the rake-angled surfaces mate to ensure latching of the rotatable member relative to the two vertebral support structures when the rotatable member is in the second orientation.

22. The nucleus replacement implant of claim 12, wherein each vertebral support structure includes an outer contact surface configured to physically engage a respective vertebral endplate when the nucleus replacement implant is disposed within the intervertebral disc nucleus space with the rotatable member in the second orientation.

23. The nucleus replacement implant of claim 22, wherein each outer contact surface of the vertebral support structures includes at least one structure projecting therefrom to facilitate physical engagement of the vertebral support structure with a respective vertebral endplate when the nucleus replacement implant is disposed within the intervertebral disc nucleus space with the rotatable member in the second orientation.

24. The nucleus replacement implant of claim 23, wherein the at least one structure projecting from each outer contact surface comprises at least one spike configured to penetrate the respective vertebral endplate, thereby ensuring positioning of the nucleus replacement implant within the intervertebral disc nucleus space when the rotatable member is in the second orientation.

25. The nucleus replacement implant of claim 12, wherein the rotatable member resides within a centrally-disposed chamber formed in the elastic body, and the centrally-disposed chamber is cross-shaped and comprises intersecting horizontally oriented and vertically oriented chambers, and wherein the rotatable member is in the first orientation when positioned within the horizontally oriented chamber, and is in the second orientation when positioned within the vertically oriented chamber, and wherein an inner wall of the elastic body defines the cross-shaped, centrally disposed chamber comprising the horizontally oriented chamber and the vertically oriented chamber, and comprises inward projections which assist in maintaining the rotatable member in one of the first orientation and the second orientation.

* * * * *